(12) United States Patent
Huang et al.

(10) Patent No.: US 11,087,196 B2
(45) Date of Patent: Aug. 10, 2021

(54) INSTALLATION ASSEMBLY, INSTRUMENT AND INSTALLATION METHOD FOR RADIO FREQUENCY IDENTIFICATION TAG

(71) Applicant: XERAFY (SHANGHAI) CO., LTD., Shanghai (CN)

(72) Inventors: Linlin Huang, Shanghai (CN); Zhijia Liu, Shanghai (CN)

(73) Assignee: XERAFY (SHANGHAI) CO., LTD., Shanghai (CN)

( * ) Notice: Subject to any disclaimer, the term of this patent is extended or adjusted under 35 U.S.C. 154(b) by 0 days.

(21) Appl. No.: 16/748,759

(22) Filed: Jan. 21, 2020

(65) Prior Publication Data
US 2020/0160136 A1 May 21, 2020

Related U.S. Application Data

(63) Continuation of application No. PCT/CN2017/103647, filed on Sep. 27, 2017.

(30) Foreign Application Priority Data

Jul. 24, 2017 (CN) .......................... 201710608435.8

(51) Int. Cl.
  *G06F 17/00* (2019.01)
  *G06K 19/077* (2006.01)
(52) U.S. Cl.
  CPC ... *G06K 19/07737* (2013.01); *G06K 19/0772* (2013.01)
(58) Field of Classification Search
  USPC ........................................ 235/375, 451, 492
  See application file for complete search history.

(56) References Cited

U.S. PATENT DOCUMENTS

| | | | | |
|---|---|---|---|---|
| 8,282,011 B1* | 10/2012 | Skoine | ............ | G06K 19/07758 235/492 |
| 2008/0132882 A1* | 6/2008 | DeMaria | ................ | A61B 90/90 606/1 |
| 2010/0033309 A1* | 2/2010 | Blair | ...................... | A61B 90/98 340/10.1 |
| 2014/0102136 A1* | 4/2014 | Warren | ................ | A44C 9/0061 63/1.14 |
| 2014/0131454 A1* | 5/2014 | Weisshaupt | ............ | A61B 90/90 235/492 |

(Continued)

FOREIGN PATENT DOCUMENTS

CN        102810174 A        12/2012

OTHER PUBLICATIONS

International Search Report of PCT Patent Application No. PCT/CN2017/103647 dated Mar. 28, 2018.

*Primary Examiner* — Tuyen K Vo

(57) ABSTRACT

Disclosed herein are an installation assembly (1), an instrument (2) and an installation method for a radio frequency identification tag. The installation assembly (1) comprises a first housing unit (11) mounted on the instrument (2) and a second housing unit (14) snapped-fitted with the first housing unit (11) to form a receiving space for receiving the radio frequency identification tag (13). The radio frequency identification tag (13) can be easily installed on the instrument (2) by snapping-fitting the first housing unit (11) with the second housing unit (14), thereby effectively enhancing installation efficiency and reliability of the radio frequency identification tag (13).

12 Claims, 6 Drawing Sheets

(56) References Cited

U.S. PATENT DOCUMENTS

2015/0189770 A1\* 7/2015 Loop ................ G06K 19/07764
312/223.1
2016/0128798 A1\* 5/2016 Bovet .............. G06K 19/07749
206/459.5
2018/0336381 A1\* 11/2018 Homanfar .......... G06K 7/10366

\* cited by examiner

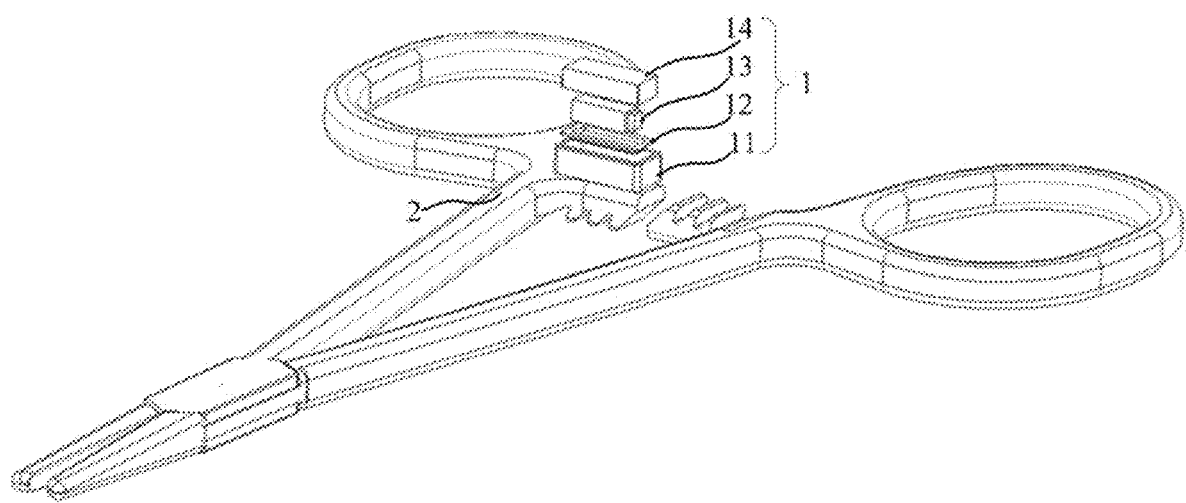
FIG. 1
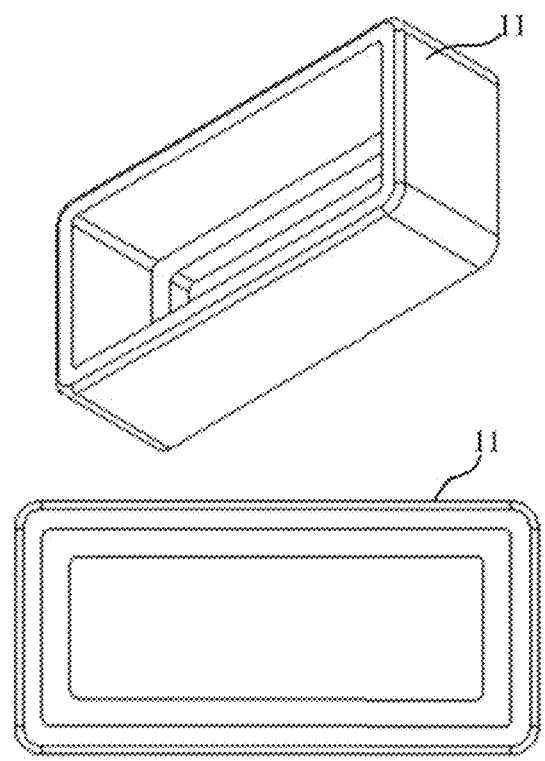
FIG. 2A
FIG. 2B

INSTALLATION ASSEMBLY, INSTRUMENT AND INSTALLATION METHOD FOR RADIO FREQUENCY IDENTIFICATION TAG

The present application is a Continuation Application of PCT Application No. PCT/CN2017/103647 filed on Sep. 27, 2017, which claims the priority to Chinese Invention Patent Application Serial No. 201710608435.8 filed on Jul. 24, 2017, entitled "INSTALLATION ASSEMBLY, INSTRUMENT AND INSTALLATION METHOD FOR RADIO FREQUENCY IDENTIFICATION TAG", the entire disclosure of which is hereby incorporated by reference.

FIELD OF THE INVENTION

The present invention relates to the field of radio frequency identification, more particular, to an installation assembly, an instrument and an installation method for a radio frequency identification tag.

BACKGROUND OF THE INVENTION

In medical industry, effective management of surgical instruments is very important. Traceability of re-processing procedures for the reusable medical instruments is a key factor to ensure that the surgical instruments are correctly re-processed. That is to say, the surgical instruments need to be subject to sterilizing, washing, cleaning, drying, checking, packing and sterilizing before reusing. Such process is performed for the purpose of avoiding spread of infection sources among patients. Traceability at instrument level can be used to indicate the ways (disassembling, immersing, cleaning, re-assembling, functionally checking and so on) for processing instruments by disinfectants.

Traceability of surgical instruments is able to improve finance and management (evaluation of inventory, repair of the instruments and management of alternative instruments, materials alarm, records of the instruments, and inventory management and the like) for the surgical instruments. It is also able to perform inventory check on the sterilization basket to reduce accident risk in the operation room.

RFID (Radio Frequency Identification) tags are typically provided on the surgical instruments to ensure identifiability and traceability of the surgical instruments. Users could readily check and trace the surgical instruments by using RFID tags.

However, in the prior arts, RFID tags cannot be readily mounted on the instruments or reliability of the mounted tags does not satisfy operational requirements on the medical instruments, thereby resulting in low installation efficiency and unsafe use of the surgical instruments.

It should be noted that the above description on background is merely used for better understanding of the background of the present invention, including information that is not known by the skilled in the art.

SUMMARY OF THE INVENTION

Provided herein are an installation assembly, an instrument and an installation method for a radio frequency identification tag, so as to at least overcome one or more problems caused by limitations and deficiencies of the relative techniques in some extent.

Other features and advantages of the present invention will become obvious by referring to the below detailed descriptions or will be obtained by practice of the present invention.

In one aspect, provided herein is an installation assembly for a radio frequency identification tag, comprising a first housing unit mounted on an instrument and a second housing unit, which together with the first housing unit forms a receiving space for receiving the radio frequency identification tag by snapping-fitting with each other.

In some embodiments, the installation assembly for a radio frequency identification tag further comprises: a metal substrate. The first housing unit has a first opening provided on the bottom thereof and a second opening provided on the top thereof. The metal substrate is disposed within and snapped-fitted with the first opening, such that it is fixed on the instrument. The second housing unit covers the second opening on the top of the first housing unit. The first housing unit, the metal substrate and the second housing unit form a sealed space.

In some embodiments, the first housing unit comprises a bottom wall and side walls coupled to the bottom wall. The first opening is disposed within the bottom wall. The metal substrate has a size greater than that of the first opening and is disposed within the first housing unit and abutted against and snapped-fitted with the bottom wall.

In some embodiments, a receiving slot for receiving the radio frequency identification tag is formed on the metal substrate.

In some embodiments, the receiving slot has a depth greater than or equivalent to the thickness of the bottom wall of the first housing unit.

In some embodiments, the first and the second housing units are made of poly-ether-ether-ketone.

In some embodiments, the metal substrate is welded to the instrument by electric resistance welding or laser welding.

In some embodiments, the bottom of the first housing unit is fixed on the instrument.

In some embodiments, the bottom of the first housing unit is adhered to the instrument, or fixed on the instrument by using bolts or rivets.

In some embodiments, the sectional area of the first housing unit is greater than that of the second housing unit and the second housing unit is located within the first housing unit.

Alternatively, the sectional area of the first housing unit is smaller than that of the second housing unit and the second housing unit encapsulates the first housing unit.

In some embodiments, the installation assembly for a radio frequency identification tag has a structure of cuboid, cube, cylinder or irregular steric structure.

In some embodiments, the installation assembly for a radio frequency identification tag further comprises a radio frequency identification tag disposed within the receiving space formed by the first and the second housing units.

In another aspect, provided herein is an instrument, comprising an instrument body, and the installation assembly for a radio frequency identification tag as mentioned above. The installation assembly for a radio frequency identification tag is mounted on the body of instrument.

In yet another aspect, provided herein is a method for installing the installation assembly for a radio frequency identification tag on an instrument, comprising: providing a first housing unit with a first opening provided on the bottom thereof and a second opening provided on the top thereof; providing a metal substrate disposed within and snapped-fitted with the first opening; fixing the metal substrate on the instrument; placing the radio frequency identification tag within the space formed by the first housing unit and the metal substrate; providing a second housing unit which covers the second opening on the top of the first housing unit.

In some embodiments, the method further comprises filling the gap between the metal substrate and the radio frequency identification tag with a sealant or a rubber pad after placing the radio frequency identification tag within the space formed by the first housing unit and the metal substrate.

In still another aspect, provided herein is a method for installing the installation assembly for a radio frequency identification tag on an instrument, comprising: providing a first housing unit, with a first opening provided on the bottom thereof and a second opening provided on the top thereof; providing a metal substrate disposed within and snapped-fitted with the first opening, fixing the metal substrate on the instrument, providing a second housing unit, installing the radio frequency identification tag within the space formed by the second housing unit, allowing the second housing unit with the radio frequency identification tag installed therein to cover the second opening on the top of the first housing unit.

In some embodiments, a receiving space formed by snapping-fitting the first housing unit which is installed on the instrument with the second housing units is used for receiving the radio frequency identification tag, such that the radio frequency identification tag can be readily installed on the instrument by the snapped-fitted first and second housing units, thereby enhancing installation efficiency of the radio frequency identification tag.

In the embodiments as described herein, the first and the second housing units are made of poly-ether-ether-ketone, such that the surgical instruments with the radio frequency identification tags installed thereon by the method as described herein not only satisfy ISO-10993 biocompatibility criteria, but also avoid influence on identification of the radio frequency identification tags due to metal materials of the first and the second housing units.

It should be understood that, the above-mentioned and the below detailed descriptions are merely for illustration and explanation, without limiting the scope of the present invention.

BRIEF DESCRIPTION OF THE DRAWINGS

The drawings are incorporated herein as a part of the specification for illustrating the examples of the present invention and for explaining the principle of the present invention together with the specification. It is obvious that the drawings merely show some examples of the present invention and other drawings obtained based on these drawings are apparent for the skilled in the art.

FIG. 1 shows an exploded view illustrating an installation assembly for a radio frequency identification tag which is installed on the instrument according to the first embodiment as described herein.

FIGS. 2a and 2b respectively show a side-view and a top-view structural schematic diagrams for the first housing unit according to the first embodiment as described herein.

DETAILED DESCRIPTION OF THE INVENTION

Figure 3A:
FIGS. 3a and 3b respectively show a side-view structural schematic diagram for the metal substrate from different angles according to one embodiment as described herein.

Several aspects of the invention are described below in details by reference to appended drawings and specific embodiments. The skilled in the art should understand that the embodiments are set forth to provide an illustration, rather than limit the scope of the present invention. The scope of the present invention is limited by the appended claims.

The features, structures or characteristics as described herein can be combined in one or more embodiments. A number of details are described below for the purpose of better understanding of the present invention. The skilled in the art would understand that the present invention can be practiced without one or more of specific details, or by using other methods, components, devices, steps and the like. Under other conditions, the common methods, devices, operations in the art are not described in detail.

The flow charts in the drawings are illustrative, which do not comprise all of the operations/steps, and it is not necessary to perform operations/steps in the described orders. For example, some operations/steps can be exploded, or can be combined or combined in part. Therefore, the actual practice sequence can be varied as needed.

The terminology used herein is for the purpose of describing particular embodiments only and is not intended to be limiting of the invention. As used herein, the singular forms "a", "an" and "the" are intended to include the plural forms as well, unless the context clearly indicates otherwise.

In the embodiments as described herein, the installation assembly for a radio frequency identification tag comprises a first housing unit that is mounted on an instrument and a second housing unit, which together with the first housing unit forms a receiving space for receiving the radio frequency identification tag by snapping-fitting with each other.

Since the first and the second housing units are snapped-fitted with each other, the radio frequency identification tag can be readily installed, thereby enhancing installation efficiency of the radio frequency identification tag.

The first housing unit can be disposed on the instrument by various ways, and the first and the second housing units can be engaged together by various snapping-fitting ways. Preferable embodiments are described in detail as below.

Example 1

Disposing the First Housing Unit on the Instrument

Referring to FIG. 1, the installation assembly 1 for a radio frequency identification tag comprises a metal substrate 12, in addition to a first and a second housing units 11 and 14.

Referring to FIGS. 2a and 2b (wherein FIG. 2a is a side-view of the first housing unit 11 and FIG. 2b) is a top-view of the first housing unit 11), the first housing unit 11 has a first opening provided on the bottom thereof and a second opening provided on the top thereof. When installing, the metal substrate 12 is disposed within the first opening on the bottom of the first housing unit 11 and snapped-fitted with the first opening, such that the metal substrate 12 is fixed on the instrument 2. The second housing unit 14 covers the second opening on the top of the first housing unit 11, such that the first housing unit 11, the metal substrate 12 and the second housing unit 14 form a sealed space with the radio frequency identification tag 13 placed therein.

The metal substrate 12 is welded to the instrument 2 by electric resistance welding or laser welding, which adapts for the situation where the instrument 2 is a metal instrument, such as a surgical instrument. The advantages produced by fixing the metal substrate 12 on the instrument 2 via welding means include (1) simply and readily fixing the metal substrate 12 on the instrument 2, and (2) needing no extra welding point. In the prior arts, it needs to provide an extra welding point on the metal substrate of the installation assembly when welding the metal substrate of the installation assembly on the metal instrument, thereby resulting in increased volume of the installation assembly and inconvenience for installing on the metal instrument and using the metal instrument. In the embodiments of the installation assembly for a radio frequency identification tag as described herein, the metal substrate 12 is welded on the instrument 2 and then the second housing unit 14 is allowed to cover the first housing unit 11. Welding is performed within the metal substrate 12 without providing an extra welding point on the metal substrate 12, such that the installation assembly for a radio frequency identification tag is further miniaturized and it is convenient for using the instrument with the said installation assembly installed thereon.

More particularly, the first housing unit 11 comprises a bottom wall and side walls coupled to the bottom wall, with the first opening disposed within the bottom wall of the first housing unit. The metal substrate 12 has a size greater than the size of the first opening on the bottom wall of the first housing unit 11. The metal substrate 12 is disposed within the first housing unit 11 and abutted against and snapped-fitted with the bottom wall.

Figure 3B:
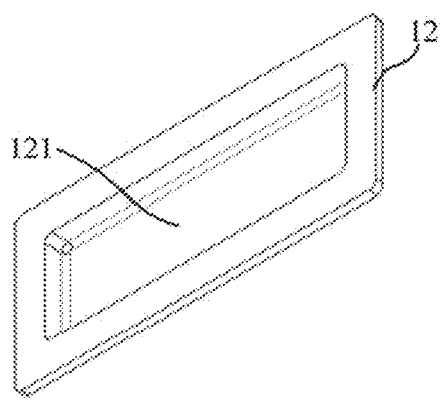

Referring to FIGS. 3a and 3b, a receiving slot 121 for receiving the radio frequency identification tag 13 is formed on the metal substrate 12. Preferably, the size of the receiving slot 12 matches the size of the radio frequency identification tag 13 to ensure that the radio frequency identification tag 13 can be fixed when placing it in the receiving slot 12.

In the illustrative embodiments as described herein, when placing the radio frequency identification tag 13 in the receiving slot 121, the gap between the radio frequency identification tag 13 and the receiving slot 121 can be sealed by filling with sealants or rubber pads, to avoid waggle of the radio frequency identification tag 13.

In the illustrative embodiments as described herein, the depth of the receiving slot 121 is greater than or equivalent to the thickness of the bottom wall of the first housing unit 11. In this embodiment, by allowing the depth of the receiving slot 121 to be greater than or equivalent to the thickness of the bottom wall of the first housing unit 11, the bottom wall of the receiving slot 121 on the metal substrate 12 contacts with the instrument 2 for ease of performing welding when placing the first housing unit 11 on the instrument 2.

In the embodiments as described herein, the first and the second housing units 11 and 14 are made of poly-ether-ether-ketone, so as to avoid influence on identification of the radio frequency identification tag, due to use of metal materials. Meanwhile, for the surgical instruments, use of poly-ether-ether-ketone would satisfy ISO-10993 biocompatibility criteria. For the surgical instruments, the metal substrate 12 may be preferably made of 316L stainless steel, which satisfies ISO-10993 biocompatibility criteria.

Example 2

Disposing the First Housing Unit on the Instrument

Figure 4:
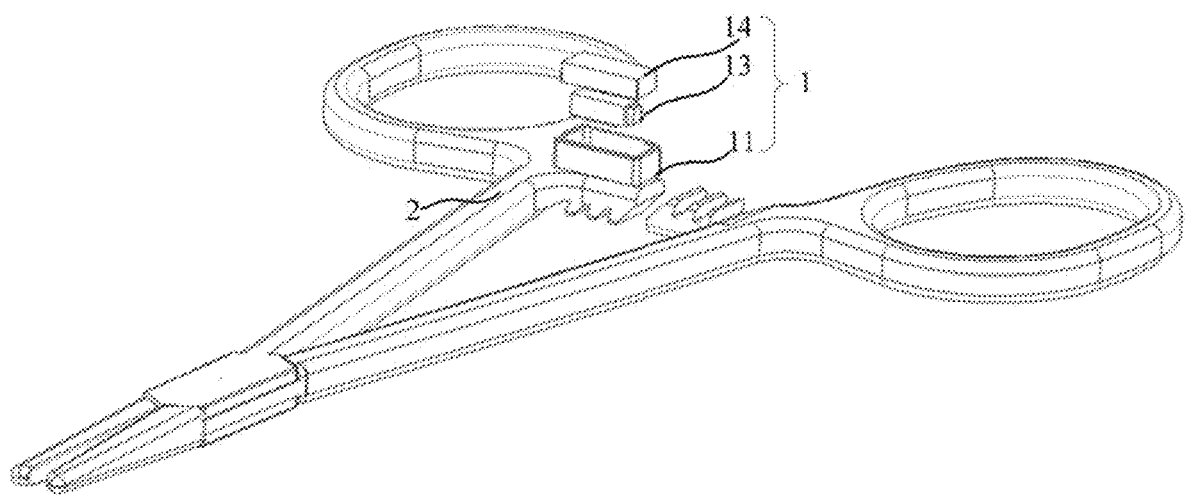
FIG. 4 shows an exploded view illustrating an installation assembly for a radio frequency identification tag which is installed on the instrument according to the second embodiment as described herein.

Referring to FIG. 4, the installation assembly 1 for a radio frequency identification tag comprises a first housing unit 11 the bottom of which is fixed on an instrument 2 and a second housing unit 14. This example has advantages including: fixing the first housing unit 11 on the instrument 2 without providing other components (e.g., the metal substrate as mentioned in Example 1).

Figure 5A:
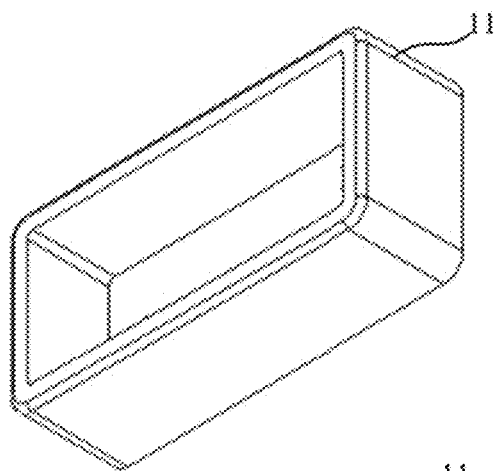
FIGS. 5a and 5b respectively show a side-view and a top-view structural schematic diagrams for the first housing unit according to the second embodiment as described herein.
Figure 5B:
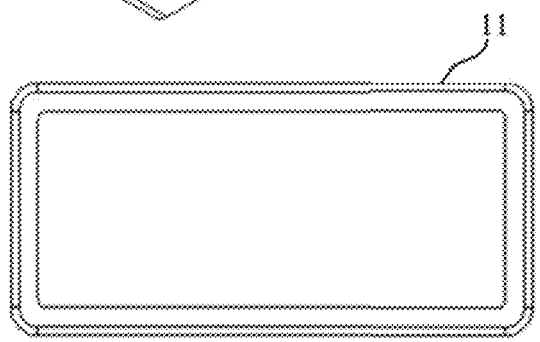

In this Example 2, referring to FIGS. 5a and 5b (wherein FIG. 5a is a side-view of the first housing unit 11, and FIG. 5b is a top-view of the first housing unit 11), the first housing unit 11 comprises a bottom wall and side walls coupled to the bottom wall. When the bottom of the first housing unit 11 is adhered to the instrument 2, no installation hole is provided on the bottom wall of the first housing unit 11 as shown in FIGS. 5a and 5b. When the bottom of the first housing unit 11 is fixed to the instrument 2 by using bolts or rivets, an installation hole can be provided on the bottom wall of the first housing unit 11.

Figure 6A:
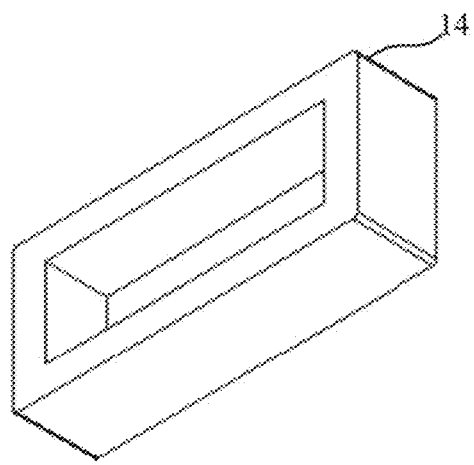
FIGS. 6a and 6b respectively show a side-view and a top-view structural schematic diagrams for the second housing unit according to one embodiment as described herein.
Figure 6B:
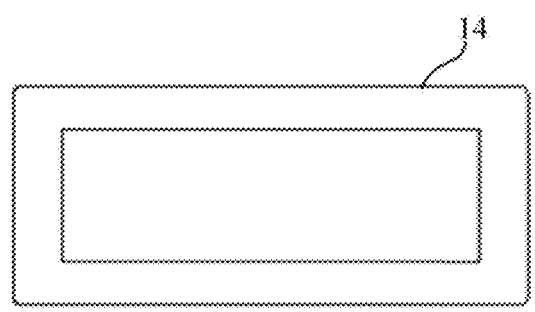

Referring to FIGS. 6a and 6b, it shows the structure of the second housing unit 14 as described herein (wherein FIG. 6a is a side-view of the second housing unit 14 and FIG. 6b is a top-view of the second housing unit 14), the second housing unit comprises a substrate and side walls coupled to the substrate. The ways for snapping-fitting the first housing unit 11 with the second housing unit 14 will be described as below.

In the embodiments as described herein, the first housing unit 11 is snapped-fitted with the second housing unit 14 by the following ways.

Snapping-Fitting Way I:

The sectional area of the first housing unit 11 is greater than that of the second housing unit 14, such that the second housing unit 14 is within the first housing unit 11 when snapping-fitting the second housing unit 14 with the first housing units 11.

Snapping-Fitting Way II:

The sectional area of the first housing unit 11 is smaller than that of the second housing unit 14, such that the first housing unit 11 is encapsulated by the second housing unit 14 when snapping-fitting the second housing unit 14 with the first housing units 11.

It should be noted that the second housing unit 14 can be entirely or partially located within the cavity formed by the first housing unit 11 by the Snapping-Fitting Way I, and the first housing unit 11 can be entirely or partially located within the cavity formed by the second housing unit 14 by the Snapping-Fitting Way II.

Taking the Snapping-Fitting Way I as an example, the technical solution of the embodiments as described herein will be described as below.

Figure 7:
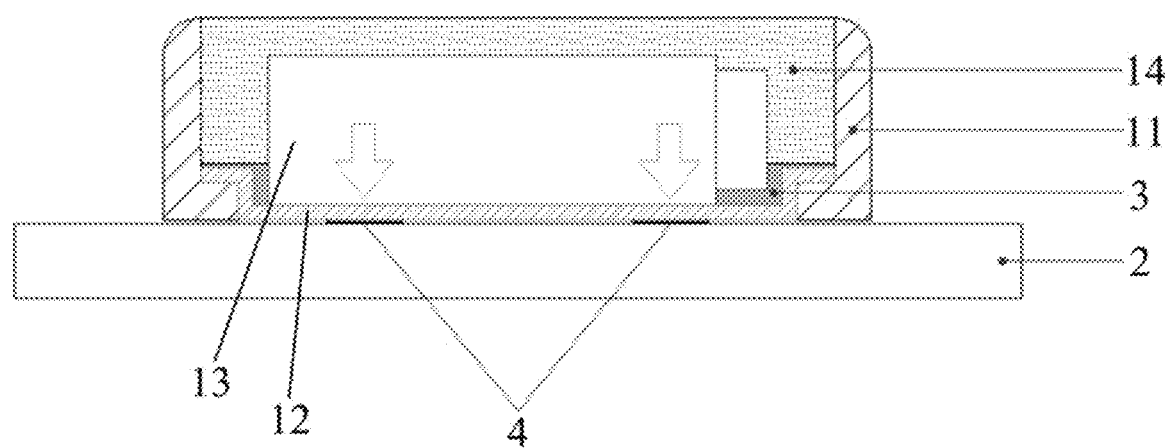
FIG. 7 shows a sectional view of the installation assembly for a radio frequency identification tag formed after assembling the first housing unit, the metal substrate, the radio frequency identification tag and the second housing unit, according to one embodiment as described herein.

Referring to FIG. 7, it is a sectional view of the installation assembly for a radio frequency identification tag formed based on the configuration means as described in Example 1 and the above Snapping-Fitting Way I. In the example as shown in FIG. 7, the metal substrate 12 is snapped-fitted with the first housing unit 11 and meanwhile welded on the instrument 2. Reference numeral 4 in FIG. 7 is the welded joint. The radio frequency identification tag 13 is disposed within the receiving slot formed in the metal substrate 12 and the gap between the receiving slot and the radio frequency identification tag 13 is filled with the sealant 3 or rubber pads. After the second housing unit 14 is snapped-fitted with the first housing unit 11, the second housing unit 14 is entirely within the first housing unit 11.

In addition, for the structure of the installation assembly for a radio frequency identification tag as mentioned in Example 1, the corresponding installation method is provided as below.

Figure 8:
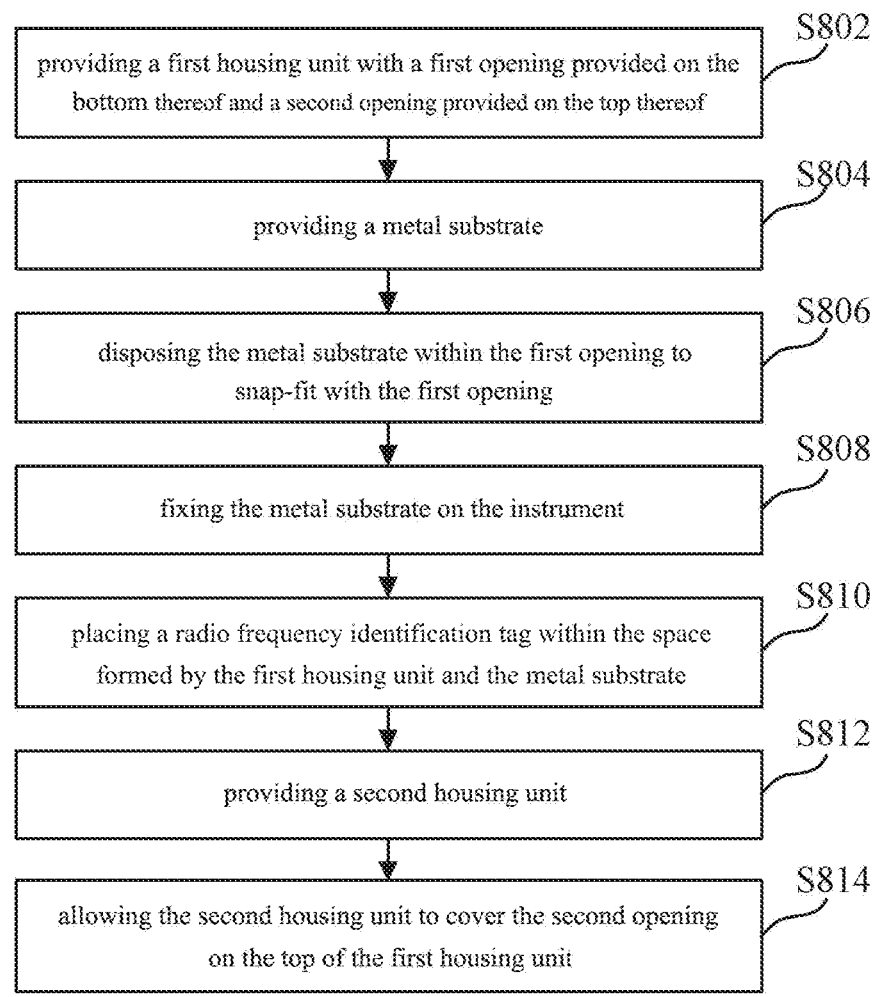
FIG. 8 shows a schematic flow chart for installing the installation assembly for a radio frequency identification tag on the instrument according to the first embodiment as described herein.

Installation Method I:

Referring to FIG. 8, a method for installation of the installation assembly for a radio frequency identification tag on an instrument according to the first embodiment comprises:

Step S802: providing a first housing unit with a first opening provided on the bottom thereof and a second opening provided on the top thereof;

Step 804: providing a metal substrate;

Step 806: disposing the metal substrate within the first opening and allowing the metal substrate to snap-fit with the first opening, Step 808: fixing the metal substrate on the instrument, Step 810: placing the radio frequency identification tag into the space formed by the first housing unit and the metal substrate, Step 812: providing a second housing unit, Step 814: allowing the second housing unit to cover the second opening on the top of the first housing unit.

In the illustrative embodiment, the metal substrate can be welded on the instrument by electric resistance welding or laser welding.

In some embodiments, the method as described herein further comprises filling the gap between the metal substrate and the radio frequency identification tag with the sealant or rubber pad, after placing the radio frequency identification tag into the space formed by the first housing unit and the metal substrate.

In this example, the sealant or the rubber pad filled into the gap between the metal substrate and the radio frequency identification tag will ensure leak tightness between the radio frequency identification tag and the metal substrate, thereby avoiding waggle of the radio frequency identification tag.

Figure 9:
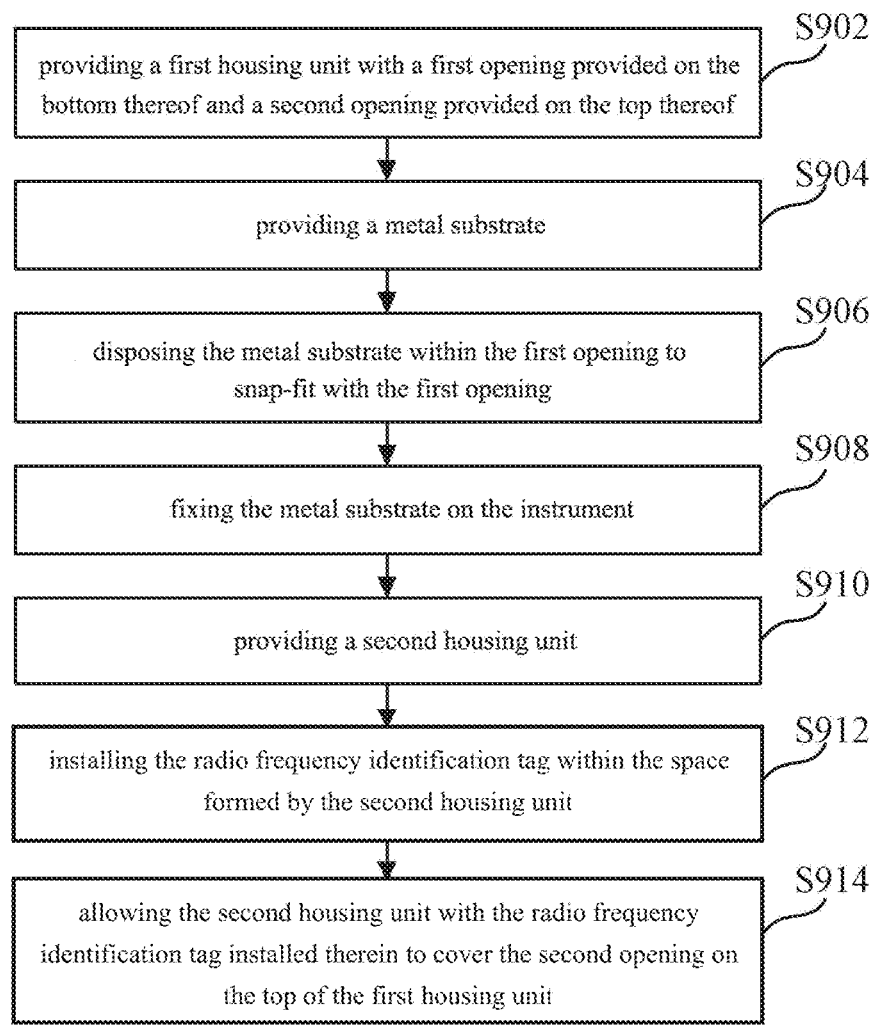
FIG. 9 shows a schematic flow chart for installing the installation assembly for a radio frequency identification tag on the instrument according to the second embodiment as described herein.

Installation Method II:

Referring to FIG. 9, a method for installation of the installation assembly for a radio frequency identification tag on an instrument according to the second embodiment comprises:

Step S902: providing a first housing unit with a first opening provided on the bottom thereof and a second opening provided on the top thereof, Step S904: providing a metal substrate, Step S906: disposing the metal substrate within the first opening and allowing the metal substrate to snap-fit with the first opening, Step S908: fixing the metal substrate on the instrument, Step S910: providing a second housing unit, Step S912: installing the radio frequency identification tag within the space formed by the second housing unit, Step 914: allowing the second housing unit with the radio frequency identification tag installed therein to cover the second opening on the top of the first housing unit.

It should be noted that the instrument as mentioned in the above examples may be a surgical instrument and the first housing unit 11 and the second housing unit 14 may be made of poly-ether-ether-ketone. The metal substrate 12 is preferably made of 316L stainless steel and can be installed by means of welding. The first and the second housing units will not block radio frequency signal and meanwhile they satisfy ISO-10993 biocompatibility criteria, such that the installation assembly for a radio frequency identification tag can be subject to the processing procedures for surgical instruments, such as washing, sterilization and disinfection and the like.

The instrument as mentioned in the above examples will not be limited to the surgical instrument, which may be implants, alternatives for implants, prostheses, tools and any other objects which are intended to be labeled to ensure their identification and traceability and are associated with industry, computer, railway, cars, ships, aviation and the like.

It should be noted that the installation assembly for a ratio frequency tag as described herein is not limited to be rectangle, which may be square, cylinder, or irregular steric structure. That is to say, the first and the second housing units may have any shapes as long as both of them can be snapped-fitted with each other.

It should be noted that although several modules or units for performing actions are described above in detail, they are not intended to limit the present invention. The functions and features of two or more modules or units as mentioned above can be combined in one module, and vice versa, the functions and features of one module as mentioned above can be divided into several modules or actions.

The skilled in the art should understand that the illustrative embodiments as described herein can be implemented by software, or software in combination with necessary hardware. Therefore, the technical solution of the embodiments of the present invention can be embodied by the way of software that may be stored in a non-volatile memory medium (such as CD-ROM, flash disk, mobile hard disk drive and the like) or internet, and may comprise several commands to instruct a computing device (such as a PC, a server, a touch control terminal, or a network device) to perform the method as described herein.

The skilled in the art would easily consider other embodiments based on the specification and after practicing the present invention. Any variations, uses or adaptable changes for the present invention follow the general principle of the present invention and include common knowledge and common means in the art. The embodiments as described herein are merely for illustration and the scope and spirit of the present invention are limited by the appended claims.

The foregoing is provided for illustration, and does not intend to limit the present invention. Any changes and modifications for the above embodiments come within the scope of the present invention.

The invention claimed is:

1. An installation assembly for a radio frequency identification tag, comprising:
   a first housing installed on an instrument and a second housing which is snapped-fitted with the first housing to form a receiving space for receiving a radio frequency identification tag therein;
   the installation assembly further comprises a metal substrate, wherein:
   the first housing has a first opening provided on the bottom thereof and a second opening provided on the top thereof;
   the metal substrate is disposed within and snapped-fitted with the first opening and fixed on the instrument;
   the second housing covers the second opening of the first housing; and
   the first housing, the metal substrate and the second housing form a sealed space;
   wherein the first housing comprises a bottom wall with the first opening provided therein and side walls coupled to the bottom wall, and wherein the metal substrate has a size greater than that of the first opening, which is disposed within the first housing and abutted against and snapped-fitted with the bottom wall;
   wherein the metal substrate is welded on the instrument by electric resistance welding or laser welding;
   wherein the first housing is fixed on the instrument on the bottom thereof.

2. The installation assembly for a radio frequency identification tag of claim 1, wherein a receiving slot is formed on the metal substrate, for receiving the radio frequency identification tag.

3. The installation assembly for a radio frequency identification tag of claim 2, wherein the receiving slot has a depth greater than or equivalent to the thickness of the bottom wall of the first housing.

4. The installation assembly for a radio frequency identification tag of claim 1, wherein the first and the second housings are made of poly-ether-ether-ketone.

5. The installation assembly for a radio frequency identification tag of claim 1, wherein the first housing is adhered to the instrument on the bottom thereof, or the first housing is fixed on the instrument on the bottom thereof by bolts or rivets.

6. The installation assembly for a radio frequency identification tag of claim 1, wherein:
   the sectional area of the first housing is greater than that of the second housing and the second housing is within the first housing; or
   the sectional area of the first housing is smaller than that of the second housing and the first housing is encapsulated within the second housing.

7. The installation assembly for a radio frequency identification tag of claim 1, wherein the installation assembly is a cuboid, a cube, a cylinder or has an irregular steric structure.

8. The installation assembly for a radio frequency identification tag of claim 1, further comprising a radio frequency identification tag which is disposed within the receiving space formed by the first and the second housings.

9. An instrument, comprising:
   an instrument body, and
   the installation assembly for a radio frequency identification tag of claim 1, which is mounted on the instrument body.

10. A method for installing an installation assembly for a radio frequency identification tag on an instrument, comprising:
    providing a first housing, with a first opening provided on the bottom thereof and a second opening provided on the top thereof; wherein the first housing is fixed on the instrument on the bottom thereof;
    providing a metal substrate, which is disposed within and snapped-fitted with the first opening; wherein the first housing comprises a bottom wall with the first opening provided therein and side walls coupled to the bottom wall, and wherein the metal substrate has a size greater than that of the first opening, which is disposed within the first housing and abutted against and snapped-fitted with the bottom wall;
    fixing the metal substrate on the instrument; wherein the metal substrate is welded on the instrument by electric resistance welding or laser welding;
    placing a radio frequency identification tag within the space formed by the first housing and the metal substrate;
    providing a second housing; and
    allowing the second housing to cover the second opening on the top of the first housing.

11. The method of claim 10, further comprising filling the gap between the metal substrate and the radio frequency identification tag with a sealant or a rubber pad after placing a radio frequency identification tag within the space formed by the first housing and the metal substrate.

12. A method for installing the installation assembly for a radio frequency identification tag on an instrument, comprising:
    providing a first housing, with a first opening provided on the bottom thereof and a second opening provided on the top thereof; wherein the first housing is fixed on the instrument on the bottom thereof;
    providing a metal substrate, which is disposed within and snapped-fitted with the first opening; wherein the first housing comprises a bottom wall with the first opening provided therein and side walls coupled to the bottom wall, and wherein the metal substrate has a size greater than that of the first opening, which is disposed within the first housing and abutted against and snapped-fitted with the bottom wall;
    fixing the metal substrate on the instrument; wherein the metal substrate is welded on the instrument by electric resistance welding or laser welding;
    providing a second housing;
    placing a radio frequency identification tag within the space formed by the second housing; and
    allowing the second housing with the radio frequency identification tag placed therein to cover the second opening on the top of the first housing.

* * * * *